United States Patent [19]

Woodland

[11] 4,249,660
[45] Feb. 10, 1981

[54] POTATO SORTING APPARATUS

[75] Inventor: Sylvester L. Woodland, Wilder, Id.

[73] Assignee: Aquasonics, Inc., Wilder, Id.

[21] Appl. No.: 37,861

[22] Filed: May 10, 1979

[51] Int. Cl.³ .............................................. B07C 5/00
[52] U.S. Cl. .................................. 209/555; 209/587; 209/590; 209/906; 209/644
[58] Field of Search ........ 209/906, 539, 934, 576–582, 209/586, 587, 588, 590, 555; 250/223 R; 406/53, 55; 73/574, 576, 579, 589, 632, 598, 600

[56] References Cited

U.S. PATENT DOCUMENTS

| 3,121,324 | 2/1964 | Cowan | 310/336 X |
| 3,177,382 | 4/1965 | Green | 310/334 |
| 3,382,975 | 5/1968 | Hoover | 209/906 X |
| 3,608,715 | 9/1971 | Snyder | 209/590 |

FOREIGN PATENT DOCUMENTS

1132416  6/1962  Fed. Rep. of Germany .......... 209/590

*Primary Examiner*—Allen N. Knowles
*Attorney, Agent, or Firm*—Warren F. B. Lindsley

[57] ABSTRACT

A hydraulic actuated agricultural product sorting apparatus employing a hopper introducing products into a fluid flow which carries them into two counter-rotating spirals mounted side by side which align and merge the products and then moves them in line into a singulator which uniformly spaces them prior to their movement through an inspection station which inspects them and signals a gating means for sorting the products according to the signals received from the inspection station.

14 Claims, 19 Drawing Figures

POTATO SORTING APPARATUS

BACKGROUND OF THE INVENTION

The processing of fruits and vegetables for marketing in various forms still involves a considerable amount of hand labor which adds very significantly to the cost of the finished product. Typically the operations involves may include grading according to size, inspection and sorting of defects such as external spots or internal voids, peeling, quartering, slicing, etc. The labor involved is tedious work which quickly becomes a drudgery; it is slow and time consuming and it requires a relatively large amount of floor space. Furthermore, hand methods are not always as effective as they might be, as, for example, in the case of inspection for internal voids or spoilage in potatoes.

In the interest of reducing the cost of such foods in the marketplace, eliminating the drudgery involved in food processing and producing a better product, it is desirable that a higher degree of automation be achieved in these operations. More specifically, there is a need for automatic equipment with a capability for handling, inspecting and sorting food products such as potatoes in a rapid and efficient manner.

SUMMARY OF THE INVENTION

In accordance with the invention claimed, improved equipment and apparatus are provided for use in the automatic handling, inspection and sorting of raw fruits or vegetables including, in particular, potatoes.

It is, therefore, one object of the present invention to provide improved apparatus for the automatic processing of raw fruits and vegetables.

Another object of this invention is to provide such apparatus with a capability for segregating and dispatching individual pieces of such products along a conveyor line in a manner which facilitates subsequent inspection and sorting operations.

A further object of this invention is to provide such apparatus with a capability for accurately positioning the individual pieces at various stages of conveyence through the equipment as required for accurate and effective inspection.

A still further object of this invention is to provide in such apparatus a capability for detecting externally visible defects.

A still further object of this invention is to provide in such apparatus a capability for detecting internal voids not visually apparent.

A still further object of this invention is to provide in such apparatus a capability for automatically sorting the individual pieces into two or more segregated paths of departure according to quality or different types of defects.

A still further object of this invention is to provide such apparatus with a capability for reducing the hand labor content, the required floor space, and the time consumed in these operations and thereby to reduce the cost of the finished food products.

Further objects and advantages of the invention will become apparent as the following description proceeds, and the features of novelty incorporated in the invention will be pointed out with particularity in the claims annexed to and forming a part of this specification.

BRIEF DESCRIPTION OF THE DRAWING

The present invention may be more readily described by reference to the accompanying drawing, in which.

DESCRIPTION OF THE PREFERRED EMBODIMENT

Figures 1, 2, 3, 4, 6:
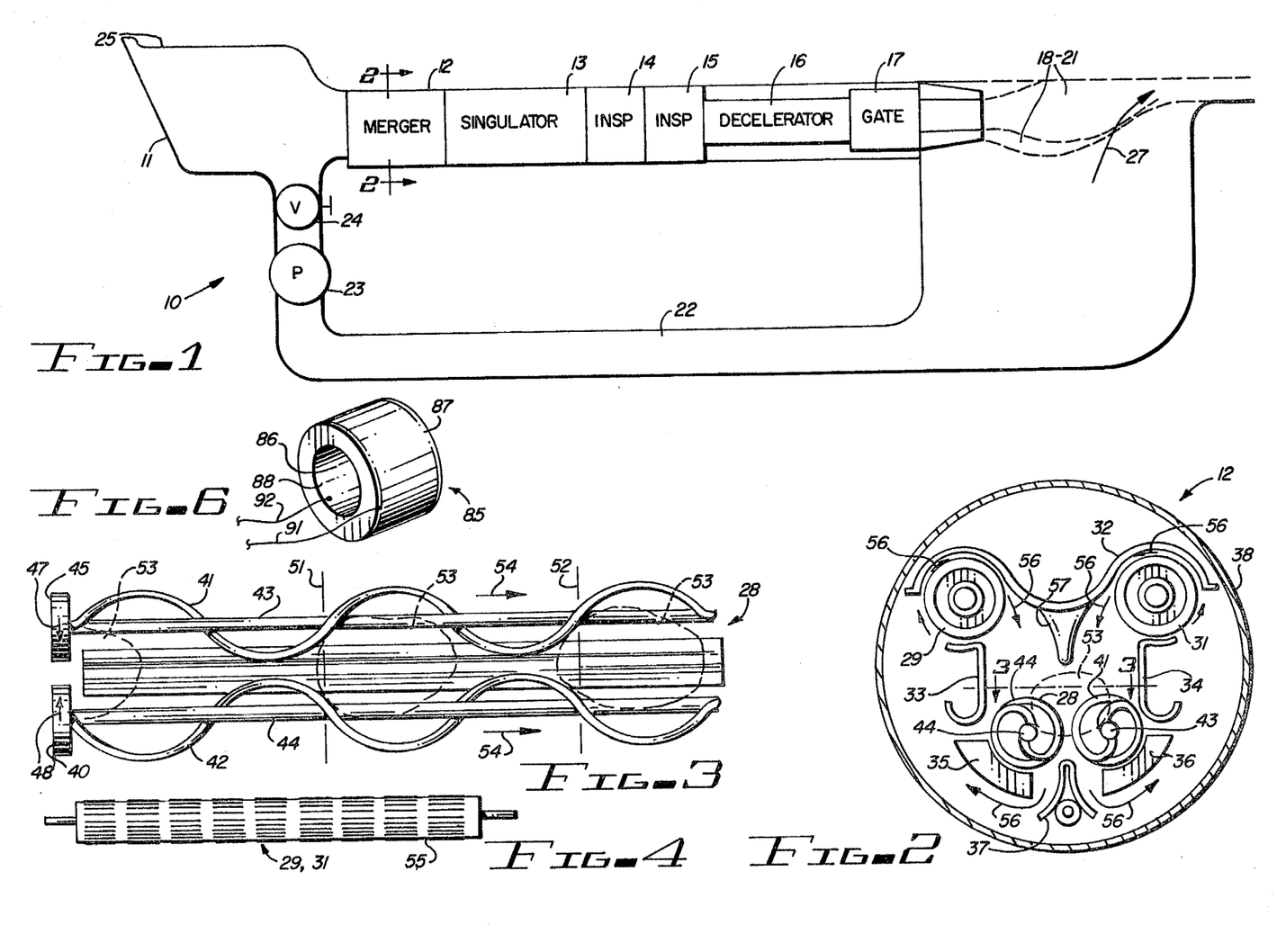
FIG. 1 is a functional block diagram of the handling, inspection and sorting system of the invention.
FIG. 2 is a cross-sectional end view of the apparatus comprising the merger stage of the system of FIG. 1 as viewed along line 2—2 of that Figure.
FIG. 3 is a cross-sectional top view of the merger stage as viewed along line 3—3 of FIG. 2.
FIG. 4 is a perspective side view of an impeller rotor employed as a component of the merger stage.
FIG. 6 is a simplified perspective view of the ultrasonic transducer employed at the first inspection station of the system of FIG. 1.

Referring more particularly to the drawing by characters of reference, FIG. 1 illustrates the potato sorting system 10 of the invention, the system comprising a hopper 11, a merger stage 12, a singulator stage 13, a first inspection station 14, a second inspection station 15, a decelerator or diffuser 16, a gating stage 17, delivery channels 18-21, water return channel 22, pump 23 and valve 24. The entire system 10 is filled with water which is caused by pump 23 to flow through valve 24 and thence through merger stage 12, singulator stage 13, inspection stages 14 and 15, decelerator 16, gating stage 17 and back through channel 22 to pump 23.

The potatoes or other products to be sorted are loaded into hopper 11 through its open top 25. The water carries the potatoes from hopper 11 into the merger stage 12 in which they become aligned and at least partially separated. From the merger stage 12 the potatoes pass single file into the singulator stage 13 which further acts upon the moving product in a manner which causes the individual potatoes to be uniformly spaced apart. A minimum separation distance is required for the proper functioning of the inspection stations 14 and 15 and for the proper operation of the gating stage 17. As the potatoes pass through inspection station 14 they are inspected sonically for internal voids or spoilage; as they then pass through the second inspection station 15 they are inspected optically for visible surface defects. Finally, the gating stage 17 ushers each potato into the appropriate delivery channel 18, 19, 20 or 21 in accordance with the findings of the inspection stations 14 and 15. Thus, for example, those with internal voids are directed into channel 18, those with visible defects into channel 19, and those with no defects into channel 21. An additional inspection station might be added if desired, to check for undersized potatoes. These could be directed into the remaining channel 20.

The channels 18-21 are made of closely spaced rods or mesh so that they will retain the potatoes or other product but will permit the flowing water to pass through into return channel 22. Excess water continually introduced into the system 10 produces an overflow 27 which carries the sorted potatoes from channels 18-21 into collection bins not shown in the drawing.

Details of the interior construction of merger stage 12 are shown in FIGS. 2-4. Merger stage 12 as shown in FIG. 2 comprises a dual-spiral conveyor 28, first and second rotary impellers 29 and 31, an upper baffle 32, left and right side baffles 33 and 34, left and right lower baffles 35 and 36 and center lower baffle 37. A cylindrical housing 38 contains the parts already enumerated as well as the water which passes through it.

Conveyor 28, as shown in FIGS. 2 and 3 comprises two counter-rotating spirals 41 and 42 mounted side-by-side and parallel to each other. They are longitudinally positioned in housing 38. Spirals 41 and 42 have the same number of turns per unit of length but they are wound in opposite directions, i.e. spiral 42 is wound like a right-hand screw while spiral 41 is wound like a left-hand screw. Spiral 41 is secured at its ends to a straight rod 43 which passes longitudinally through spiral 41 along the axis of spiral 41. Spiral 42 is similarly mounted to a second straight rod 44. Mounted at the left-hand end of the rod 43 and secured thereto is a gear 45; an identical gear 46 is secured to the left-hand end of rod 44. Gear 45 is rotated by an external gear train in the direction of arrow 47. Gear 46 is coupled to the same gear train and is caused thereby to rotate at the same angular velocity but in the opposite direction. In the instant angular position of the spirals 41 and 42 shown in FIG. 3 both spirals pass directly above their respective rods 43 and 44 at positions 51 and 52. As the spirals 41 and 42 are turned in the directions 47 and 48 respectively, by the gears 45 and 46, the positions 51 and 52 move steadily to the right. As this occurs, the individual potatoes shown as ghost images 53 are nudged by the advancing edges of the spirals. The spacing of the potatoes is in this manner caused to approximate the period of the spirals, which is equal to the distance between positions 51 and 52. Because the water flow as indicated by the arrows 54 tends to move the potatoes in the same direction as the counter-rotating spirals 41 and 42, the mechanical action of the spirals is softened in terms of the forces applied to the potatoes as they are carried along.

To assure the effectiveness of the spiral conveyor 28 in moving the potatoes in the manner just described, it is necessary to provide a means for holding the potatoes against the rods 43 and 44. Hydraulic forces for this purpose are provided by the impellers 29 and 31 with the aid of the baffles 32-37. The impellers 29 and 31 are identical. As shown in FIG. 4 they are cylindrical in form with radially extending fins 55. Impellers 29 and 31 are mounted side-by-side above spirals 41 and 42 in mutually parallel orientation. The circularly contoured baffle 32 extends around the upper surfaces of impellers 29 and 31 with clearance provided between the outer surfaces of the impellers 29 and 31 and the under surface of the baffle 32 to permit the rotation of the impellers and the passage therebetween of induced water currents 56 which continue to flow downward toward the top surfaces of the spirals 41 and 42. The side baffles 33 and 34 which are mounted respectively below impellers 29 and 31 direct the currents 56 downward against the potatoes or other product 53 urging them downward against the rods 43 and 44. Flowing around the product 53, the currents 56 pass laterally through the spirals 41 and 42, through passages between the lower baffles 35, 36 and 37 and then finally turn upward along the inner surfaces of housing 38 to be recirculated by the impellers 29 and 31.

Baffle 32 has a downwardly extending ridge 51' and baffle 37 has the form of an upwardly extending ridge. These special contours have the purpose of producing smooth laminar flow of the currents 56 in two counter-circulating loops, one of which encircles impeller 29 and spiral 42, the other encircling impeller 31 and spiral 41. The smooth laminar flow of these currents prevents turbulence and erratic motion of the potatoes as they move through the merger stage 12.

Figure 5A:
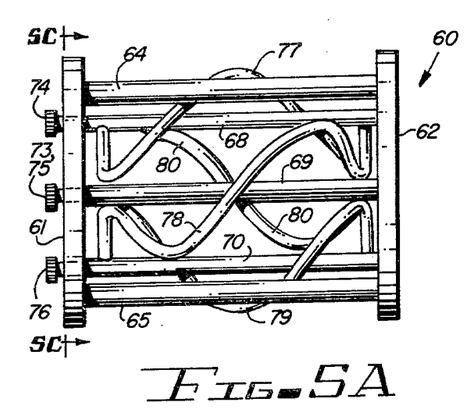
FIG. 5A is a perspective side view of the internal mechanism of the singulator stage of the system of FIG. 1, the singulator mechanism shown here in the center-open condition.
Figure 5B:
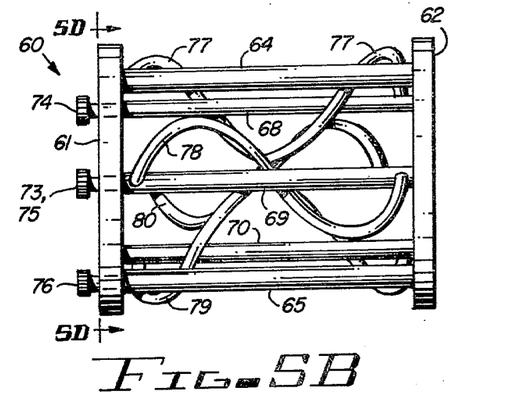
FIG. 5B is a perspective side view of the singulator mechanism of FIG. 5A, shown here in the center-closed condition.
Figure 5C:
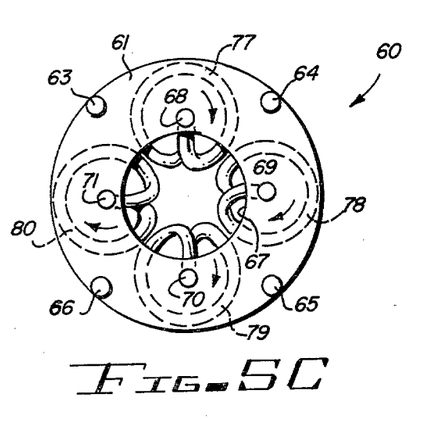
FIG. 5C is an end view of the singulator mechanism of FIGS. 5A and 5B, shown in the center-open condition.

While the merger stage 12 thus tends to separate and space the product 53, a somewhat more positive positioning action is provided by the singulator stage 13, the interior mechanism of which is shown in FIGS. 5A-5D. FIGS. 5A and 5B show the same mechanism from the same side view but at different times in the operating cycle. As shown in both FIGS. 5A and 5B and in their respective end views 5C and 5D, the singulator mechanism 60 comprises two open-centered circular end plates 61 and 62 supported in mutually opposite parallel relationship by four support posts 63, 64, 65 and 66. The posts 63-66 are mutually parallel and have their ends secured at quadrature positions just inside the outer circumferences of plates 61 and 62. The center opening 67 of plate 61 is circular with a diameter approximately half that of the outer circumference of plate 61. Plate 62 has a center opening which is identical to opening 67.

Also mounted between plates 61 and 62 are four spiral-support rods 68, 69, 70 and 71. The spiral-support rods are rotationally mounted at their ends to the plates 61 and 62 and they extend through plate 61 for coupling by means of gears 73-76.

Four spirals, 77, 78, 79 and 80 are mounted, one each, to the four rods, 68, 69, 70 and 71 respectively. The four spirals 77-80 are identical dimensionally and all have the same sense, but they are instantaneously at quadrature positions rotationally. Thus, in the instant positions shown in FIG. 5C, spiral 77 has its near end directed downward, spiral 78 has its near end directed to the left, spiral 79 has its near end directed upward, and spiral 80 has its near end directed to the right. The near ends are thus all directed toward the center so that they effectively close off the opening 67 at the left-hand end of the view of FIG. 5A. It may also be noted from FIG. 5A that each of the spirals 77–80 makes a complete turn, i.e. 360 degrees, from end to end about its respective rod, 68–71, with the result that the central opening between the rods 68–71 is closed at both ends and open in the center.

Figure 5D:
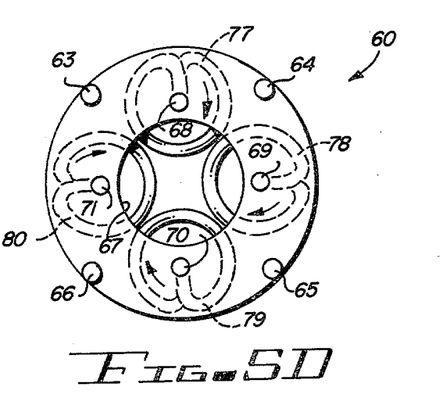
FIG. 5D is an end view of the singulator mechanism of FIGS. 5A and 5B shown in the center-closed condition.

In the views of FIGS. 5B and 5D each of the four spirals 77–80 has rotated 180 degrees in a clockwise direction so that the near and far ends in the view of FIG. 5D are directed outward. The space between the rods 68–71 is in this case open at both ends and closed at the center.

As the spirals 77–80 thus continue to turn sychronously in a clockwise direction the central passage between the rods 68–71 is periodically opened first at the left-hand end to receive a potato or other product. As rotation continues, the opening moves steadily toward the center of the mechanism 60, at which point both ends are closed and the received potato is completely enveloped and enclosed. Further rotation causes the opening to move on toward the right until an opening occurs at the right-hand end of mechanism 60 whereupon the potato is discharged into the first inspection station 14.

With appropriate dimensioning of the mechanism 60 the amount of product received will be limited to a single potato or other sorted unit, so that a single potato is dispatched at the desired instant into the inspection station.

At inspection station 14 the potatoes pass through the sonic transducer 85 of FIG. 6. Transducer 85 comprises a cylindrical ring of piezo-electric material. In the first implementation the outer diameter of the transducer 85 was six inches, the concentric cylindrical opening 86 through the center had a diameter of four and seven-eighths inches, and the length was three inches. The outer cylindrical surface 87 and the inner cylindrical surface 88 are coated with an electrically conductive material. Electrical conductors 91 and 92 are attached, respectively, to the outer and inner conductive surfaces 87 and 88. The conductors 91 and 92 are connected to a high-frequency power source which is tuned to a frequency near the natural or resonant frequency of the transducer 85. When the high frequency source is energized the transducer vibrates mechanically at the source frequency, the source frequency being at least partially dependent upon the natural frequency of the transducer 85 as affected by the surrounding media, including the water flowing through the center opening 86 and the potatoes or other products which are carried by the flowing water.

A potato that is sound with no internal voids or spoilage transmits the sonic waves in approximately the same manner as does the surrounding water so that no disruption in the operation of the transducer 85 occurs when such a product passes through. If there are internal defects, however, there will be a frequency shift and a change in the impedance the transducer offers to the high-frequency source. Specifically, in the first implementation of the invention an internal void in a potato produced an increase in frequency and a reduction in the power drawn by the transducer. Electronic circuits monitoring the electrical operation of the transducer detect these changes in transducer operation and control the operation of the gating stage as necessary to direct the defective potatoes into the appropriate output channel, 18–21.

Figure 7A:
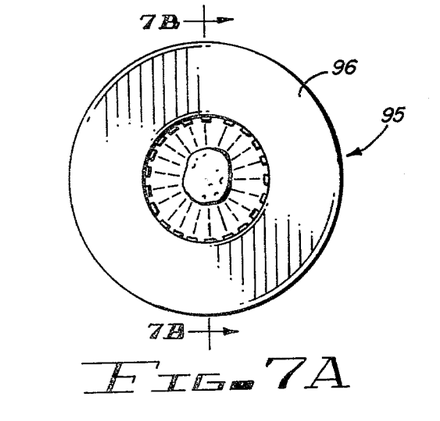
FIG. 7A is a cross-sectional end view of the optical inspection ring employed at the second inspection station of the system of FIG. 1.
Figure 7B:
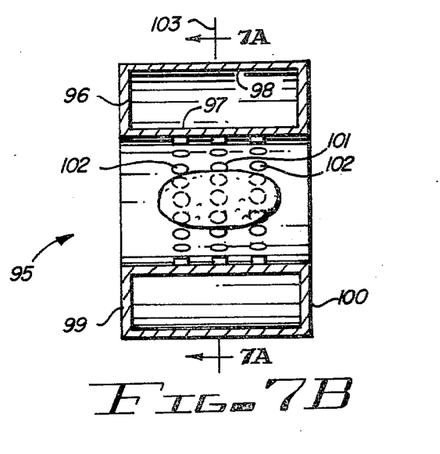
FIG. 7B is a cross-sectional side view of the inspection ring of FIG. 7A as viewed along line 7B—7B of that Figure.

At inspection station 15 the potatoes pass through the optical inspection ring 95 of FIGS. 7A and 7B. Ring 95 comprises a ring-shaped housing 96 of approximately the same shape and dimensions as those of the transducer 85 of FIG. 6. The housing 96, however, is not a solid structure. The inner and outer cylindrical walls 97 and 98 together with the disc-shaped end plates 99 and 100 define an enclosure for electrical wiring connected to photo-sensors 101 and light sources 102 which are mounted on the inner cylindrical surface of the housing 96. Approximately twenty optical sensors 101 are mounted about a circle defined by the intersection of a plane 103 passing through the housing 96 perpendicularly bisecting its cylindrical axis. The light sources 102 are similarly spaced about two circles, one on either side of the circle of photo-sensors. Both the photo-sensors 101 and the light sources 102 are directed toward the center of the ring 96. When there is no potato or other object passing through the ring, the light sources 102 supply light to the photo-sensors 101 on the opposite side of the circle. If a potato with a clear surface passes through, its light-colored surface reflects light to the sensors 101 from adjacent light sources 102. If the surface has dark spots, however, one or more of the sensors 101 will experience a momentary reduction in the amount of light energy received. Electronic circuits connected to the photo-sensors 101 detect the momentary reduction in light intensity and trigger the gating circuits as necessary to direct the defective potato into the appropriate channel 18–21.

The electronic circuits which respond to the transducer 85 and to the photo-sensors 101 will be described in a later part of the specification.

Figure 8:
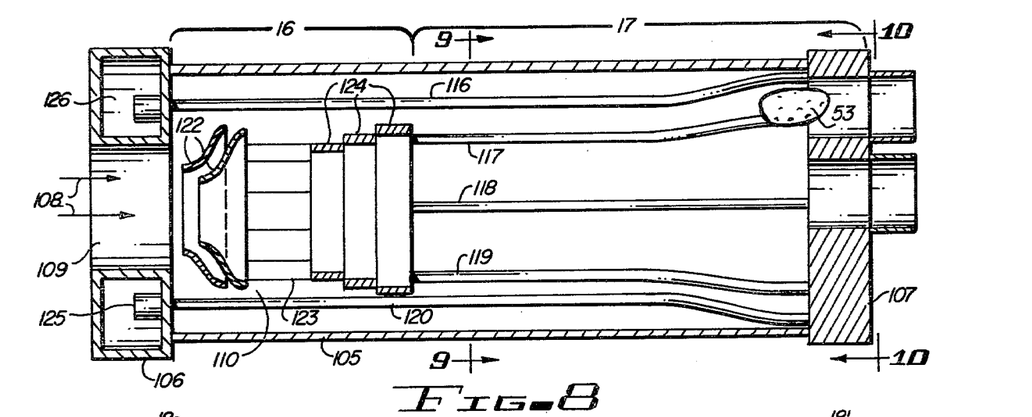
FIG. 8 is a cross-sectional side view of the diffuser and the gating stage of the system of FIG. 1.

The diffuser 16 and the gating stage 17 as shown in FIG. 8 are housed in a common cylindrical shell 105. An annular manifold 106 is secured at the left-hand or inlet end of the shell 105 and a gating plate 107 is secured at the outlet end to the right. Water 108 enters shell 105 through an opening 109 which has a diameter approximately equal to the diameters of the center openings through the inspection stations 14 and 15. Upon entering the larger diameter interior of shell 105 the water velocity decreases abruptly. To achieve this abrupt transition without producing turbulence, the decelerator assembly 110 is positioned immediately downstream from the opening 109. Surrounding the decelerator assembly 110 and forming a cylindrical cage coaxially aligned with shell 105 are the gating tubes 111–120. The manifold 106, plate 107, shell 105 and the tubes 111–120 along with solenoid valves and electronic control circuits comprise the gating stage 17.

The decelerator assembly 110 comprises a pair of nested conical sections 122 opening downstream from the inlet at opening 109, a cylindrical open cage 123, and a set of nested short cylindrical sections 124. The cylindrical sections are of successively increased diameters from left to right. The cage 123 secures the conical sections 122 at the left to the cylindrical sections 124 at the right or downstream end of the decelerator assembly 110. The controlled diversion of water from a smaller to a larger cross-sectional flow area as afforded by the conical sections 122 and the cylindrical sections 124 assures a smooth and laminar transition to the reduced water-flow velocity required for effective directional control of the product in gating stage 17.

Figures 9, 10:
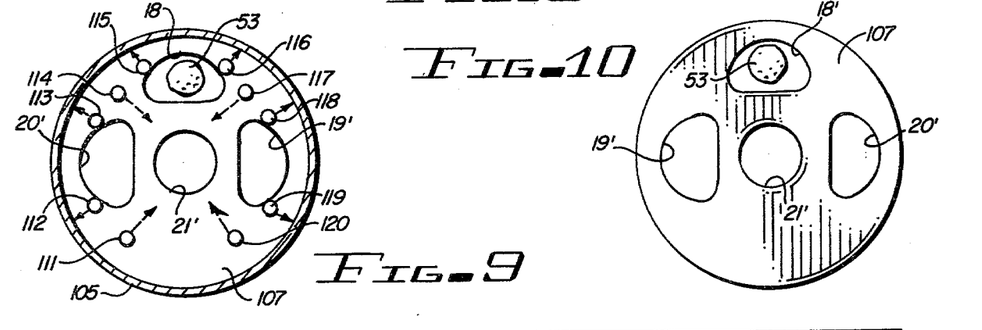
FIG. 9 is a cross-sectional end view of the gating stage of FIG. 8 as seen along line 9—9 of that Figure.
FIG. 10 is a cross-sectional end view of the gating stage of FIG. 8 as seen along line 10—10 of that Figure.

The gating tubes 111-120 are secured at the right-hand end of gating stage 17 to plate 107, their ends sealed off by their attachment in a circular pattern to plate 107 as shown in FIG. 9. At their left-hand ends the tubes 111-120 are supported by manifold 106 which they penetrate for connection to four solenoid valves 125-128, two of which are indicated in FIG. 8. The manifold 106, the solenoid valves 125-128 and their connections to lines 111-120 are shown diagrammatically in FIG. 11. A pump, not shown in the drawing, supplies water under pressure to manifold 106 through a port 131 shown in FIG. 11. Inside manifold 106 the pressurized water enters the valves 125-128 through valve inlets 132-135, respectively. Each of the valves 125-128 directs water to one or the other of two outlet ports, each of which is connected to one or two of the gating tubes 111-120.

Figure 11:
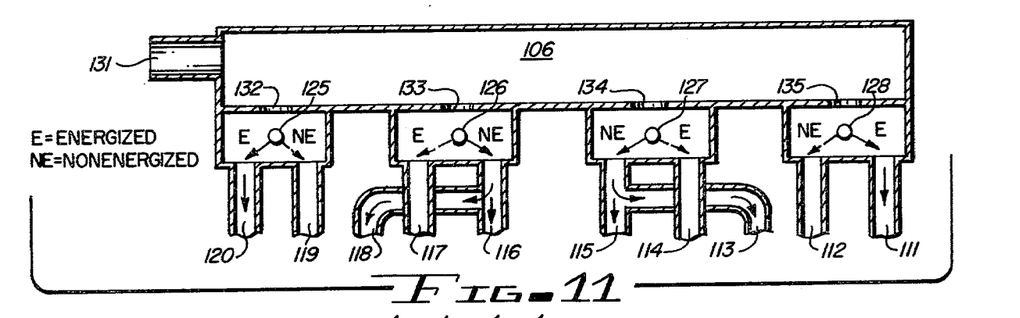
FIG. 11 is a diagrammatic representation of the solenoid valves utilized in the control of the gating stage of FIGS. 8-10.

The energized and non-energized positions of each of the valves 125-128 are indicated by the arrows labeled E and NE, respectively, in FIG. 11. Thus, valve 125 directs flow into tube 120 in its energized condition and into tube 119 in its non-energized condition; valve 126 selects tube 117 when energized and tubes 116 and 118 when not energized; valve 127 selects tube 114 when energized and tubes 113 and 115 when not energized; and valve 128 selects tube 111 when energized and tube 112 when not energized. In each case the tubes selected by the non-energized valve conditions are tubes which direct water radially outward while those selected by the energized valve conditions are tubes which direct water inward toward the passing product.

Figure 12:
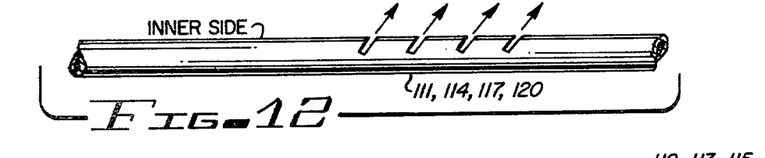
FIG. 12 is a side view of one of the set of gating tubes incorporated in the gating stage of FIG. 7.
Figure 13:
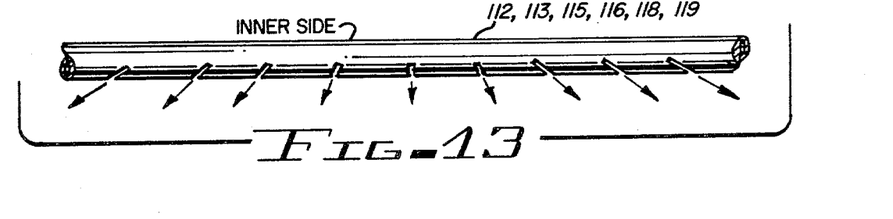
FIG. 13 is a side view of one of the set of decelerating tubes of the gating stage of FIG. 7.

The manner in which the cuts are made in the gating tubes 111-120 is illustrated in FIGS. 12 and 13.

As indicated in FIG. 12, the cuts in tubes 111, 114, 117 and 120 are located on the radially inner sides of the tubes and are distributed over half the length of each tube on the downstream end of the tube. The cuts, in this case, are uniformly inclined in a downstream direction.

In the case of tubes 112, 113, 115, 116, 118 and 119, as shown in FIG. 13, the cuts are distributed over the full length of the tubes and are located on the radially outward side of each tube. The inclination of the cuts in each tube is in an outward and upstream direction at the inlet end and radially outward and downstream at the outlet end. The inclination changes gradually and progressively from upstream to downstream along the length of each tube.

Tubes 111, 114, 117 and 120 provide the "nudging" or directive action on the passing products by means of water jets directed selectively at the product. This nudging action is most effectively applied just before the product reaches the plate 107. It is for this reason that the cuts in these tubes cover only the downstream portions of the tubes. As the product moves through this region an appropriate combination of selected tubes 111-120 causes the individual potato or other product to be ushered through one of the openings, 18'-21' of plate 107.

Tubes 112, 113, 115, 116, 118 and 119 perform dual fashions. The upstream inclination at the inlet end aids in the deceleration of the water as it enters the deceleration stage 16. Farther downstream, the downstream inclination with appropriate selection of individual tubes causes currents to be set up which aid in the ushering of the product into the desired opening 18', 19', 20' or 21'.

As an illustration of the manner in which the tubes 111-120 are selectively activated to direct the product into a desired opening of plate 107, FIGS. 11 and 9 utilize solid-line arrows to indicate selected solenoid valve positions and water jet directions which cause the potato 53 to be directed into opening 18'. As indicated by the solid arrows adjacent valves 125 and 128, these valves are energized to select tubes 111 and 120 and to block flow to tubes 112 and 119. The solid arrows adjacent solenoid valves 126 and 127 indicate these valves are not energized and supplying water to tubes 113, 115, 116 and 118 with no flow into tubes 114 and 117. In FIG. 9 the selected tubes have their flow and direction indicated by solid-line arrows while for the unselected tubes broken-line arrows indicate what the flow direction would be had these tubes been selected.

It will now be recognized from FIG. 9 that the resultant of the inwardly directed water jets from tubes 111 and 120 is a force vector directed toward opening 18'. This force vector is aided by the upward and outward flow patterns produced by selected tubes 113, 115, 116 and 118 which in combination with the flow from tubes 111 and 120 produce two circulating currents, the currents jointly moving upward toward opening 18, then separating to the left and the right to move outward and downward along the sides of housing 105. These circulating currents carry the potato 53 upward toward opening 18. The longitudinal flow of water from inlet to outlet through gating stage 17 carries the potato 53 through opening 18' into the associated delivery channel 18.

Other combinations of selected gating tubes are employed to direct the product 53 into the other openings, 19', 20' or 21'. Thus, to direct the product 53 into opening 19', tubes 111, 114, 116, 118 and 119 are selected. For direction into opening 20', tubes 117, 120, 112, 113 and 115 are selected. If it is desired to direct the product into central opening 21', tubes 112, 113, 115, 116, 118 and 119 are selected, all of which are directed outward. The latter set of tubes is selected when none of the solenoid valves 132-135 is energized, i.e. in their non-energized positions, valve 132 selects tube 119, valve 133 selects tubes 116 and 118, valve 134 selects tubes 113 and 115, and valve 135 selects tube 112. The central opening is typically selected when there are no product defects so that the greater proportion of the product may be permitted to pass in a straight line through gating stage 17 without energizing any of the valves 132-135.

Summarizing the criteria for selection of the desired opening 18'-21' in terms of solenoid valve enerization, it is thus found that opening 18' is selected by energizing valves 125 and 128; opening 19' is selected by energizing valves 127 and 128; opening 20' is selected by energizing valves 125 and 126; and, again, opening 20' is selected by energizing none of the valves.

Figure 14A:
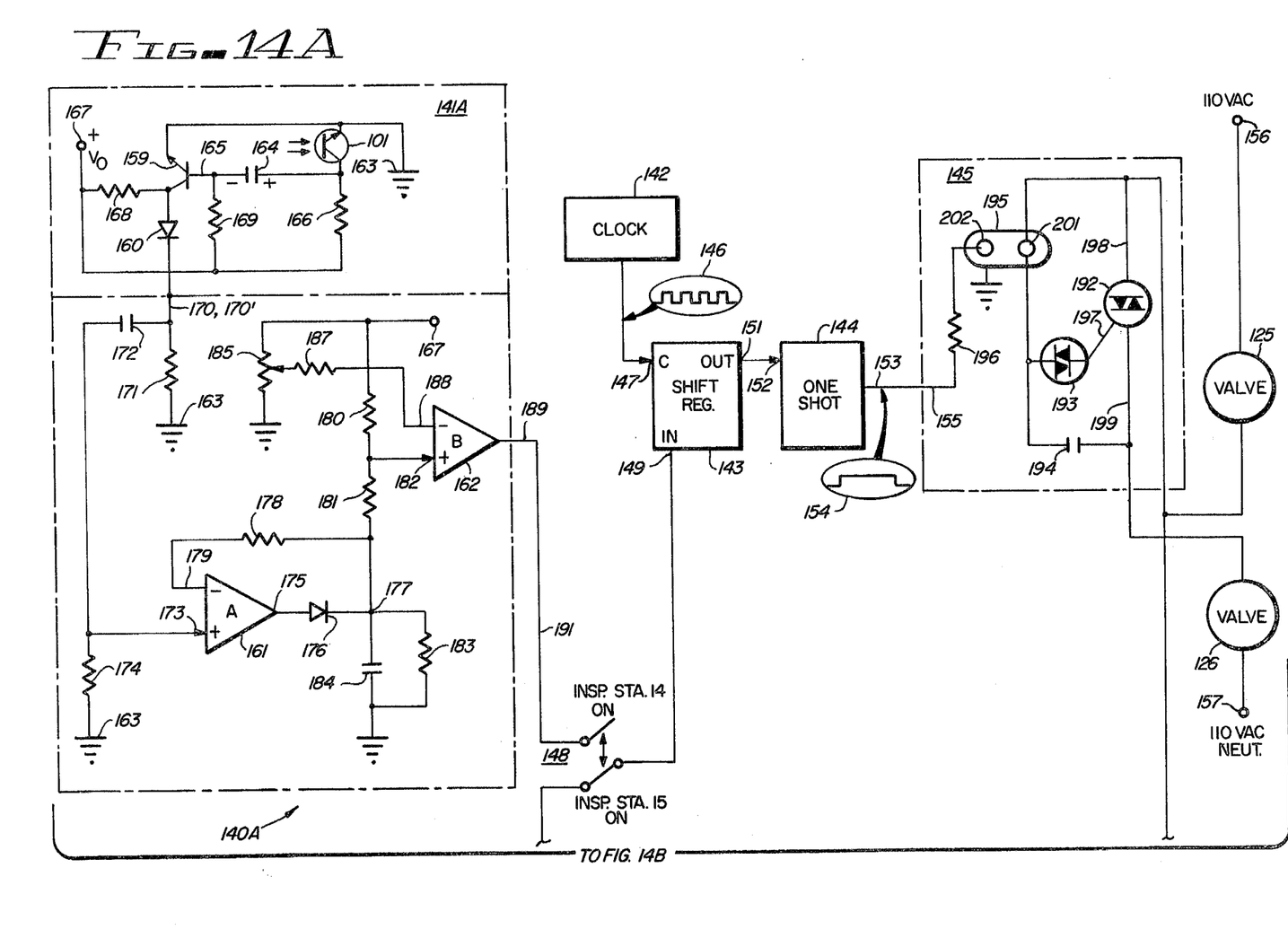
FIGS. 14A and 14B comprise the circuit diagram of the electronic control system employed to drive the solenoid valves of FIG. 11.
Figure 14B:
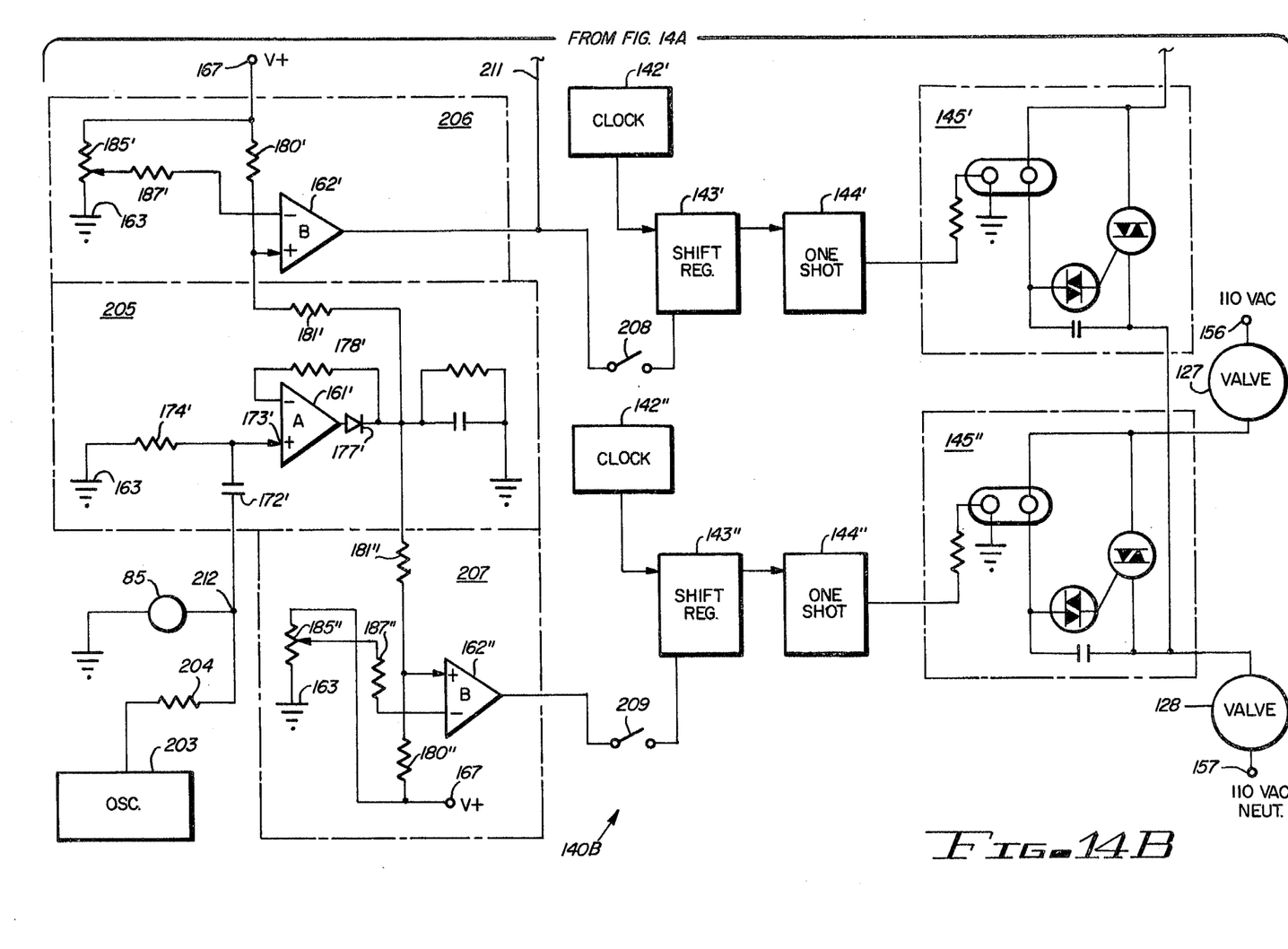

The energization of the control valves 125-128 in response to signals received from inspection stations 14 and 15 is controlled by the electronic control system 140 of FIGS. 14A and 14B.

FIG. 14A shows the part of system 140 which responds to signals from the optical inspection ring 95. This part of system 140 which is identified as subsystem 140A comprises a signal detector-amplifier 141, a clock 142, a shift register 143, a one-shot 144 and an isolated switch 145. In subsystem 140A, clock 142 supplys clock signals 146 to the clock terminal 147 of shift register 143. Detector amplifier 141 detects and amplifies signals from the sensors 101 of inspection station 15 and delivers the amplified signals through an inspection station selector switch 148 to the data input terminal 149 of shift register 143. The signal received at terminal 148 is stepped through shift register 143 through the action of clock 142, and some time later it appears at the data output terminal 151 of shift register 143. The delayed output signal is coupled to the input terminal 152 of one-shot 144. One-shot 144, responding to the relatively narrow signal received from register 143 delivers at its output terminal 153 a positive output pulse 154 of the desired width or duration. Signal 154 is coupled to the control terminal 155 of switch 145. Switch 145 responds by turning ON and remaining ON during the duration of signal 154. While switch 154 is in the ON or conductive state it energizes solenoid valves 125 and 126 which are serially connected with switch 145 across the 115 volt AC source 156. The current energizing the valves flows from source 156 through the coil of valve 125, through switch 145, and through the coil of valve 126 to the neutral terminal 157 of the AC source.

Detector-amplifier 141 incorporates an NPN transistor 159, a peak detector operational amplifier 161 and a comparator amplifier 162. Transistor 159 has its base coupled through a capacitor 164 to the anode of one of the photo-transistor sensors 101 of the optical inspection ring 95. All of the sensors 101 have their emitters connected to ground terminal 163. The collector of sensor 101 is connected by a collector resistor 166 to a positive d-c source 167. Also connected to source 167 are the collector resistor 168 and base resistor 169 of transistor 159. The collector of transistor 159 is connected to the anode of a diode 160, the cathode of which is connected to a terminal 170.

The portion of amplifier 141 including the sensor 101, transistor 159, diode 160, capacitor 164 and resistors 166, 168 and 169 comprises a sensor network 141A. One such sensor network 141A is provided in association with each of the sensors 101 of the optical inspection ring 95.

All of the terminals 170 of all the sensor networks 141A are connected to a common point 170' which is connected to ground 163 through a resistor 171, and through a coupling capacitor 172 to the non-inverting input terminal 173 of amplifier 161. Terminal 173 is also connected to ground 163 through a resistor 174. The output terminal 175 of amplifier 161 is connected to the anode of a diode 176, the cathode of which is connected to a node 177. Node 177 is connected through a resistor 178 to the inverting input terminal 179 of amplifier 161, and through a resistor 181 to the non-inverting input terminal 182 of amplifier 162. Terminal 182 is also connected through a resistor 180 to d-c terminal 167. Node 177 is also connected through a parallel network including a resistor 183 and a capacitor 184 to ground 163. A reference potentiometer 185 connected from d-c terminal 167 to ground 163 has its pick-off terminal 186 connected through a resistor 187 to the inverting input terminal 188 of amplifier 162.

In the operation of the detector-amplifier 141, light normally received by sensor 101 while no product is passing through ring 95 or when a clear unblemished potato or other product reflects light to the sensor 101 causes sensor 101 to be conductive. Current flowing from source 167 through resistor 169 into the base of transistor 159 also causes transistor 159 to be conductive. The collectors of both transistor 159 and sensor 101 are thus just a fraction of a volt above ground potential and capacitors 164 and 172 are uncharged. Terminal 173 of amplifier is at ground potential as are, consequently, the output of amplifier 175 and node 177. Because node 177 is at a near ground potential the output of amplifier 162 is also low. If a potato or other product carrying a dark surface blemish now passes through ring 95, the light received by one or more of the sensors 101 will be momentarily reduced with the result that the affected sensor 101 will momentarily turn off or exhibit reduced conductivity. As the sensor 101 is thus at least partially turned off, its collector voltage rises. As a consequence, current from source 167 flowing through resistor 166 is diverted through capacitor 164 into the base of transistor 159. Transistor 159 is not immediately affected because it is already turned on, but capacitor 164 receives a charge during the conduction of sensor 101 of the polarity indicated in the drawing. As sensor 101 subsequently turns on again when the blemished potato leaves ring 95, the charge on capacitor 164 momentarily impresses a reverse voltage across the base-emitter junction of transistor 159. Transistor 159 is turned off during the discharging of capacitors 164 so that its collector voltage rises and a positive pulse is transmitted through diode 160 and capacitor 172 to terminal 173 of amplifier 161, a positive output signal results at output terminal 175 of amplifier 161. The positive output signal produces a rapid charging of capacitor 184 through diode 176. As the output terminal 175 very quickly returns to ground potential, the blocking action of diode 176 permits capacitor 184 to hold its charge for a substantially longer period. The sustained positive signal at node 177 is sensed at terminal 182 of amplifier 162 which produces a positive signal at its output terminal 189 for as long as its input terminal 182 remains more positive than its inverting input terminal 188. The duration of this time period is adjustable over a limited range by means of the reference potentiometer 185, whereby a lower reference voltage tends to produce a pulse of increased duration at output terminal 189. When switch 148 is set to the downward position (inspection station 15 ON), the positive signal from terminal 189 is carried by line 191 to the data input terminal 149 of shift register 143.

Shift register 143 may be one of many versions which are readily available as integrated circuits from various manufacturers. On such device is available from Signetics Corporation of Sunnyvale, Calif., as a Signetics type 2532 static shift register. Characteristics of this device are described on pages 7-127 to 7-130 of the Signetics handbook published in 1972 under the title "Signetics digital linear MOS."

The device employed in the first embodiment of the invention was a 64 stage shift register. Upon each occurrence of a clock pulse at terminal 147, register 143 stores a signal in its first stage corresponding to the instantaneous signal at its data input terminal 149. Thus, if terminal 149 happens to be "low" (near ground potential) a "zero" is stored in the first stage; if terminal 149 is "high" or positive, a "one" is stored. Each successive clock signal advances the received signal ("zero" or "one") to the next stage, so that after 64 clock pulses the same signal appears at the data output terminal 151. A pattern of signals presented at imput terminal 149 is thus repeated at output terminal 151 with a time delay equal to 64 periods of the clock 142. The total delay may thus be controlled through the adjustment of the operating period of the clock 142. The delay thus provided by shift register 143 permits the potato or other product to move from its position in station 15 to the proper position in gating stage 17 before the appropriate solenoid valves 125-128 are energized.

It is also necessary to control the length of time that the solenoid valves are energized. The signal obtained from amplifier 162 is typically much too short in duration for this purpose, and the one-shot 144 is incorporated to generate a drive signal that is sufficiently long to effect the proper gating action. In the typical operation of a circuit of this type, one-shot 144 is triggered by a narrow pulse or by a rising or falling wavefront (edge) and it responds by delivering an output signal 154 controlled in its duration to the period required for sustained energization of the solenoid valves.

Both the clock 142 and the one-shot 143 may be constructed using a standard, commercially available integrated circuit known as a 555 timer. A description of the 555 timer and instructions for the connection of external components (resistors and capacitors) to form an oscillator (for use as the clock) or a one-shot is given on pages 6-49 to 6-54 of the Signetics handbook referenced earlier.

The switch 145 comprises a triac 192, a diac 193, a capacitor 194, an optical coupler 195 and a resistor 196.

The triac is a commercially available semi-conductor device which is controllable by means of its gate terminal 197 to present a high or low impedance between its power terminals 198 and 199. In its low impedance state (its ON condition), the triac passes current in either direction and exhibits a low voltage drop of two volts or less. The ON condition is set by providing a positive or negative current pulse into the gate 197.

Diac 193 is serially connected with the capacitor 194 between the gate 197 and power terminal 199 of triac 192. The diac is a threshold device which "breaks over" when its threshold voltage is exceeded. Typically, the capacitor is charged through a resistor until its voltage exceeds the threshold voltage of the diac, at which time the diac "breaks over" and the capacitor discharges into the gate of the triac turning the triac on.

The optical coupler 195 comprises a photo-resistor 201 and a light-emitting diode 202 mounted in close proximity within a proper enclosure. When the light-emitting diode (LED) is energized it emits light which falls on the photo-resistor. Illumination of the photo-resistor causes its resistance to be very significantly reduced.

In the switch 145, the photo-resistor 201 is connected from terminal 198 to gate 197 of triac 192; the LED 202 has its cathode connected to ground 163 and its anode is connected to output terminal 155 through resistor 196. A positive signal 154 at terminal 145 produces a current through resistor 196 and LED 202. The resulting illumination of photo-resistor 201 reduces its resistance so that current from terminal 198 passes through photo-resistor 201 charging capacitor 194 until diac 193 "breaks over" and the resulting current into gate 197 turns triac 192 ON to energize valves 125 and 126.

Subsystem 140B as shown in FIG. 14B provides control of solenoid valves 125, 126, 127 and 128 in response to signals received from inspection station 14. Except for the substitution of an oscillator 203 and the sonic transducer 85 with a series resistor 204 for the sensor network 141A of FIG. 14A, the circuits of subsystem 140B are the same as those of subsystem 140A, i.e. clocks 142' and 142", registers 143' and 143", one-shots 144' and 144" and switches 145' and 145" are identical to their counterparts 142, 143, 144 and 145 of FIG. 14A.

Their interconnections and operation are also the same. Amplifier 161' and its associated resistances, capacitor and diode enclosed in block 205 are identical in connections and operation to amplifier 161 and its corresponding associated parts which have the same but unprimed numeric identifications. Similarly, amplifiers 162' and 162" and their associated circuits enclosed respectively within blocks 206 and 207 are identical with amplifier 162 and its corresponding parts. The chief difference is that amplifier 161' drives two amplifiers, 162' and 162", each of which may supply signals to a shift register 143, 143' or 143". Amplifier 162' may supply signals to shift register 143' if the series switch 208 is closed, or it may supply signals to shift register 143 if switch 148 is in the upward or "Inspection Station 15 ON" position. Amplifier 162" supplies signals to shift register 143" provided switch 209 is closed.

The switchwes 148, 208 and 209 may be set to permit delivery of sorted products to any of the desired openings 18'-21'. Thus, if it is desired to direct a product sorted by station 14 to opening 20', switch 148 is set to "Inspection Station 14 ON," leaving switches 208 and 209 open. Signals from amplifier 162' are in this case delivered through line 211 and switch 148 to shift register 143 with the result that valves 125 and 126 are energized. If switch 148 is placed in the "Inspection Station 15 ON" position, with switch 208 closed and switch 209 open, signals from amplifier 162' are delivered to shift register 143' with the result that switch 145' is turned on, energizing valves 125 and 128 and thereby causing the sorted product to be directed through opening 18'. If switch 208 is opened and switch 209 is closed, signals from amplifier 162" are supplied to shift register 143" causing switch 145" to be closed with the result that valves 127 and 128 are energized. The sorted product is thus directed to opening 19'.

The detection of internal voids in the potatoes or other products passing through transducer 85 is based on a reduction in power drawn by transducer 85 from oscillator 203 which occurs when such a defect is present. With one terminal of transducer 85 connected to ground 163 and the other to oscillator 203 through the resistor 204 as shown in FIG. 14B, the reduction in power drawn by transducer 85 causes an increase in voltage at the junction 212 between transducer 85 and resistor 204. Junction 212 is connected to terminal 173' of amplifier 161' through capacitor 172', and the increased voltage at junction 212 is thus sensed by amplifier 161'. The amplified signal from amplifier 161' is delivered to amplifiers 162' and 162" for further amplification and delivery to shift registers 143, 143' and 143".

A complete and effective automatic sorting apparatus is thus provided in accordance with the stated objects of the invention, and although but a single embodiment of the invention has been illustrated and described, it will be apparent to those skilled in the art that various changes and modifications may be made therein without departing from the spirit of the invention or from the scope of the appended claims.

What is claimed is:

1. A hydraulically actuated agriculatural product sorting apparatus comprising:
   a hydraulic system for buoyantly supporting and transporting items of the product along a given path,
   a hopper containing the product connected to said system for introducing the product into said system, merging means mounted in said system for aligning each item of the product received from said hopper in sequence for moving the items along said given path, said merging means comprising two counter-rotating spirals mounted side by side and having the same number of spirals per unit of length, a singulator placed downstream from said merging means in said system for receiving in sequence said items and uniformly spacing them one from the other, at least one inspection station placed downstream from said singulator for sensing and inspecting individually each item moving along said path, gating means, at least two different hydraulic channels, said gating means actuated by said station moving the items through one of said channels depending on the results observed by said station, and means for returning at least a part of the hydraulic medium of said system discharged downstream of said hopper to substantially the beginning of said path.

2. The hydraulically actuated agricultural product sorting apparatus set forth in claim 1 wherein:
each of said spirals is secured at its ends to a straight rod which passes longitudinally through said spiral along its axis.

3. The hydraulically actuated agricultural product sorting apparatus set forth in claim 2 in further combination with:
gear means arranged at the end of each straight rods for causing said spirals to rotate at the same angular velocity but in opposite directions.

4. The hydraulically actuated agricultural product sorting apparatus set forth in claim 3 in further combination with:
hydraulic means for holding each item against the straight rods to substantially prevent erratic motion of the items through said merging means.

5. The hydraulically actuated agricultural product sorting apparatus set forth in claim 1 wherein:
said singulator comprises a plurality of spirals mounted to rotate in synchronism to periodically open a passageway at its downstream end to receive an item therebetween and to steadily move the item by the convolutes of said spiral to its upstream end and then discharge it from said singulator.

6. The hydraulically actuated agricultural product sorting apparatus set forth in claim 1 in further combination with:
a decelerator positioned in said system between said station and said gating means for decreasing the velocity of the liquid of said system.

7. The hydraulically actuated agricultural product sorting apparatus set forth in claim 6 wherein:
said decelerator comprises a plurality of successively increasing diameter cylindrical sections arranged in the direction of fluid flow in said path.

8. The hydraulically actuated agricultural product sorting apparatus set forth in claim 1 wherein:
said inspection station comprises a sonic device for sensing the internal condition of said items.

9. The hydraulically actuated agricultural product sorting apparatus set forth in claim 1 wherein:
said inspection station comprises an optical device for sensing visible surface defects of the items.

10. The hydraulically actuated agricultural product sorting apparatus set forth in claim 8 in further combination with:
a second inspection station downstream of said singulator for optically sensing and inspecting individually each item moving along said path.

11. The hydraulically actuated agricultural product sorting apparatus set forth in claim 1 wherein:
said gating means comprises a plurality of hydraulic streams directed into said path upon actuation thereof by said station for directing each item into one of said channels.

12. The hydraulically actuated agricultural product sorting apparatus set forth in claim 1 wherein:
the fluid of said hydraulic system comprises water.

13. The hydraulically actuated agricultural product sorting apparatus set forth in claim 8 wherein:
said sonic device comprises a cylindrical ring of piezo-electric material arranged in said path through which each item moves.

14. A hydraulically actuated agricultural product sorting apparatus comprising:
a hydraulic system for buoyantly supporting and transporting items of the product along a given path, a hopper containing the product connected to said system for introducing the product into said system, merging means mounted in said system for aligning each item of the product received from said hopper in sequence for moving the items along said given path, a singulator placed downstream from said merging means in said system for receiving in sequence said items and uniformly spacing them one from the other, at least one inspection station placed downstream from said singulator for sensing in inspecting individually each item moving along said path, gating means, a decelerator positioned in said system between said station and said gating means for decreasing the velocity of the liquid of said system, at least two different hydraulic channels, said gating means actuated by said station moving the items through one of said channels depending on the results observed by said station, and means for returning at least a part of the hydraulic medium of said system discharged downstream of said hopper to substantially the beginning of said path.

* * * * *